United States Patent [19]

Riley

[11] Patent Number: 4,804,142
[45] Date of Patent: Feb. 14, 1989

[54] PEST REPELLENT ARTICLES

[76] Inventor: Thomas J. Riley, 195 Kingsbury Ave., Bradford, Mass. 01835

[21] Appl. No.: 52,781

[22] Filed: May 21, 1987

Related U.S. Application Data

[63] Continuation-in-part of Ser. No. 787,614, Oct. 15, 1985, abandoned.

[51] Int. Cl.$^4$ .............................................. A61L 9/04
[52] U.S. Cl. ........................................ 239/56; 239/71; 43/131
[58] Field of Search ...................... 43/131; 239/53, 56, 239/57, 60

[56] References Cited

U.S. PATENT DOCUMENTS

| | | | |
|---|---|---|---|
| 1,769,409 | 7/1930 | Armstrong | 239/56 |
| 2,423,717 | 7/1947 | Mikina | 43/42.06 |
| 2,778,774 | 1/1957 | Buslik | 239/53 X |
| 4,277,024 | 7/1981 | Spector | 239/56 X |

FOREIGN PATENT DOCUMENTS 686329  3/1965  Italy ...................................... 239/56

Primary Examiner—Fred A. Silverberg
Assistant Examiner—Carmine Cuda
Attorney, Agent, or Firm—Edward A. Gordon

[57] ABSTRACT

A pest repellent article for dispensing a repellent composition to a receptacle or area to be protected is disclosed. The pest repellent article comprises an outer cover and an inner porous removable pest repellent composition carrier member. The repellent composition carrier is formed of a compact absorbent structure and is impregnated with a volatile pest repellent composition. The outer cover or envelope completely encloses the repellent composition carrier member and is formed of a flexible, puncturable, tearable material substantially impermeable to the repellent composition and the vapors thereof. The outer cover is releasably sealed about the inner porous pest repellent composition carrier member and can be opened to remove the inner porous repellent composition carrier member. The inner porous pest repellent composition carrier member is releasably sealed whereby the composition carrier member can be opened to release the volatile repellent composition carrier.

4 Claims, 4 Drawing Sheets

PEST REPELLENT ARTICLES

This application is a continuation-in-part of my co-pending application Ser. No. 787,614 filed Oct. 15, 1985, now abandoned.

FIELD OF THE INVENTION

This invention relates to pest repellent articles and more particularly to an improved package which serves to provide the user with an article containing a pest repellent composition ready for use to ward off insects and prevent animals from ravaging receptacles such as trash receptacles.

BACKGROUND OF THE INVENTION

Pest repellent articles and compositions are well known, moth balls deposited in a porous container being a typical example. Similarly U.S. Pat. No. 1,653,710 issued Dec. 27, 1927 discloses an antirodent preparation of an extract of coffee in solution which is impregnated in material from which bags are made. Likewise, containers formed from extracted synthetic resins sheets in which an insect repellent compound has been added is disclosed in U.S. Pat. No. 3,767,785 issued Oct. 23, 1973, the patent disclosing adding a specific organic insect repellent compound to formed sheet material to provide the desired result. An animal deterent composition comprising cinnamic aldehyde which can be applied as a coating to various objects, such as an animal stall, bandage or cast on the animal or a collar on the animal for deterring the animal from chewing or otherwise damaging the objects is disclosed in U.S. Pat. No. 4,097,607, issued June 27, 1978, to Larson. U.S. Pat. Nos. 3,857,934 issued Dec. 31, 1974, to Bernstein et al., and 3,864,468, issued Feb. 4, 1975, to Hyman et al. disclose non-porous, polymeric articles having active properties, such as antibacterial, antifungal, pesticidal, insecticidal, animal repellent, etc., in which the surface of the articles is coated with the active agent, the active agent migrates or moves throughout the body of the article to which it is applied to impart an effective level of activity throughout the body of the article and/or on a surface other than the one to which the active agent has been applied. Mosquito and insect repellents in general have been typically applied to the skin to prevent mosquito and insect bites. U.S. Pat. No. 3,590,118, issued June 29, 1971, to Conrady et al., discloses a variety of such mosquito repellent compositions in which the repellents are dissolved in interpolymer resins of alpha-beta olefinically unsaturated carbonyl monomers. The solutions are found to be slow release systems for the repellent compounds when spread and dried as films on substrates, such as the skin of humans and animals. One such known mosquito repellent disclosed by the patent is oil of citronella, a compound which has long been used to repel mosquitoes. U.S. Pat. No. 4,320,112, issued Mar. 16, 1982 discloses a composition for pest repellent receptacles wherein the active ingredient comprises a mixture of citronella oil and napthalene flakes compounded with the synthetic resin from which the trash receptacles are made. The patent discloses that receptacles made from such material can be used for storing or disposing of trash and deters animals, such as common household pets from disturbing the receptacles.

While such prior art discloses various pest repellent articles which are impregnated with a pest repellent composition, there still exists a need for a simple, inexpensive pest repellent article which is suitable for use with receptacles which have not been treated or impregnated with pest repellent compositions because of the complexity and/or cost involved in producing such an article. There is a great need, for example, for a means to render receptacles for storing or disposing trash repellent to animals, such as, common household pets, rodents and other animals which commonly rip open or overturn such receptacles, necessitating the annoying task of cleaning up the spilled contents.

Accordingly, a desirable object of the present invention is to provide an improved package which will contain and protect repellent compositions in single discrete quantities conveniently carried by an improved disposable carrier compactly carried within the package and wherein the construction and arrangement of the package enables it to be easily opened and the disposable carrier readily employed to render receptacles repellent to pests.

Another desirable object of the present invention is the provision of an improved pest repellent article of the above indicated type which is simple and inexpensive, which is compact and convenient to ship, store, and handle, which can be easily and readily opened when desired but which, while closed, will effectively protect the repellent composition from the environment and contamination as well as loss by evaporation, sublimation, dilution, leakage and the like.

A further desirable object of the invention is the provision of a pest repellent for use with non-repellent receptacles which is inexpensive so that it can be discarded with the receptacle, which is constructed to be absorbent and porous, so as to hold desired quantities of repellent compositions without adversely affecting the repellent composition carrier.

A still further desirable object of the present invention is the provision of pest repellent articles which can easily and readily be disposed upon and/or in the receptacle to be protected.

Other desirable objects and advantages of the present invention will in part appear hereinafter and will in part become apparent after consideration of the specification with reference to the accompanying drawings.

SUMMARY OF THE INVENTION

In accordance with the present invention, there is provided a pest repellent article, more particularly an improved package containing a pest repellent carrier which is constructed and arranged to enable it to be easily employed to render receptacles or areas repellent to pests. The invention contemplates a package comprising an outer cover or envelope which encloses an inner repellent composition material carrier member. The outer cover member is formed of a material which is substantially flexible and impervious to the repellent composition as well as gases and vapors. The cover material is also of a character that can be readily torn by hand to access the repellent material or punctured to release the repellent material. The repellent composition material carrier member is formed of a flexible or particulate material which is absorbent to the repellent material. The repellent material carrier in one embodiment includes an outer porous container. The invention also contemplates attaching members associated with the outer cover and/or the inner porous container for attaching said members to the receptacle to be protected.

BRIEF DESCRIPTION OF THE DRAWINGS

For a fuller understanding of the nature and desired objects of the invention, reference should be had to the following detailed description taken in connection with the accompanying drawings, wherein like reference characters refer to corresponding parts throughout the several views and wherein.

DETAILED DESCRIPTION OF THE INVENTION

Figure 1:
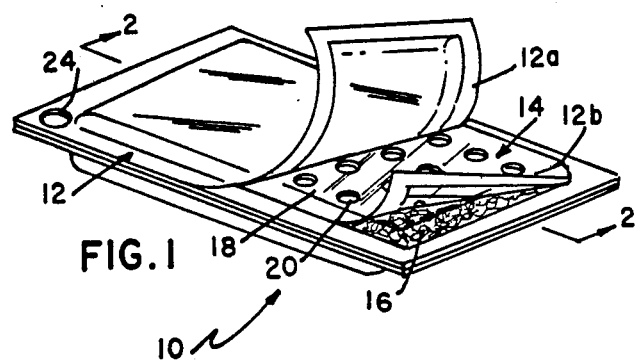
FIG. 1 is a plan view of one embodiment of the invention partially broken open to illustrate the structure and the inner repellent composition carrier.
Figure 2:
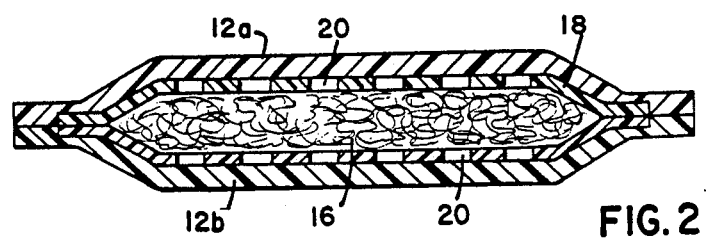
FIG. 2 is a cross-sectional view taken along the line 2—2 of FIG. 1.

Referring now to the drawings of this invention and particularly to FIGS. 1 and 2 there is illustrated generally at 10 a pest repellent article or package in accordance with the present invention. The package 10 comprises an outer cover or envelope 12 which is illustrated as being formed of two generally rectangular members 12a and 12b of the same size and sealed along their edges to provide a completely sealed outer cover 12. The outer cover 12 may be formed of various materials depending upon the form and composition of the repellent material, the main requirements being that it is not adversely affected by the repellent material; that it is relatively flexible; that it is substantially impervious to liquids; that it should be of sufficient strength to withstand the vapor pressures which may be caused by the repellent material composition contained therein and substantially impervious to gases and vapors; that it be inert to the repellent composition; and that it be readily torn or punctured by hand to permit easy access to the repellent material contained therein. Suitable materials for making the outer cover include, for example, a laminated structure of a metal foil, such as aluminum foil, which forms the outer layer and a thermoplastic film such as polyethylene, polyvinyl resin or cellulose acetate which forms the inner layer and which provides protection as well as a vapor-proof barrier while permitting the cover 12 to be heat sealed along the edges. Other materials such as cellulosic material linked with a thermoplastic film or various synthetic or plastic materials are suitable.

Disposed within the cover 12 is the repellent composition material carrier 14 which comprises an inner flexible absorbent member 16 enclosed by a porous inner cover member 18. As illustrated, the porosity of inner cover member 18 is provided by a plurality of apertures or holes 20.

The absorbent member 16 may be made of any suitable absorbent material which will not be adversely affected by the repellent material composition and which in turn will not contaminate or adversely affect the repellent material. Such materials as cellulosic or cotton fibers, and paper are suitable materials. As illustrated in FIG. 1, the absorbent member is formed of fibrous material which is sufficiently compressed to maximize absorption. Where rigidity of the porous cover 18 is not required, it can be formed of absorbent paper, for example, a wet strength type of paper which is suitable for liquid or aqueous mixtures of the repellent material since the wet strength paper will not tear or disintegrate too easily. In this manner, the repellent material carrier 14 when formed of materials of sufficient strength can be easily removed in tact and deposited in the receptacle to be protected as discussed hereinafter.

Figure 3:
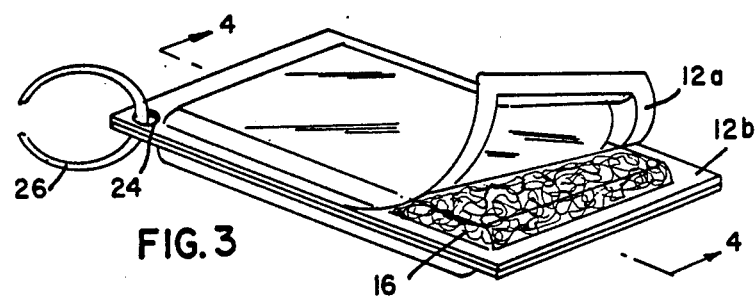
FIG. 3 is a plan view of a modified embodiment of the invention partially broken open to illustrate the structure and the inner repellent composition carrier.
Figure 4:
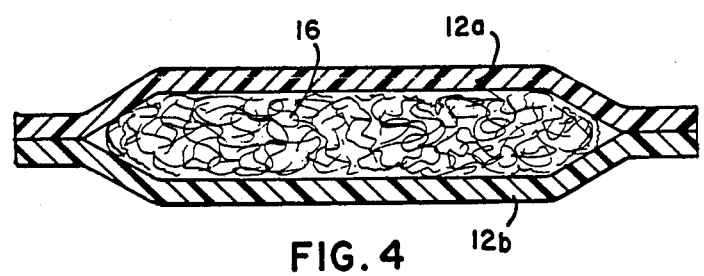
FIG. 4 is a cross-sectional view taken along the line 4—4 of FIG. 3.
Figure 5:
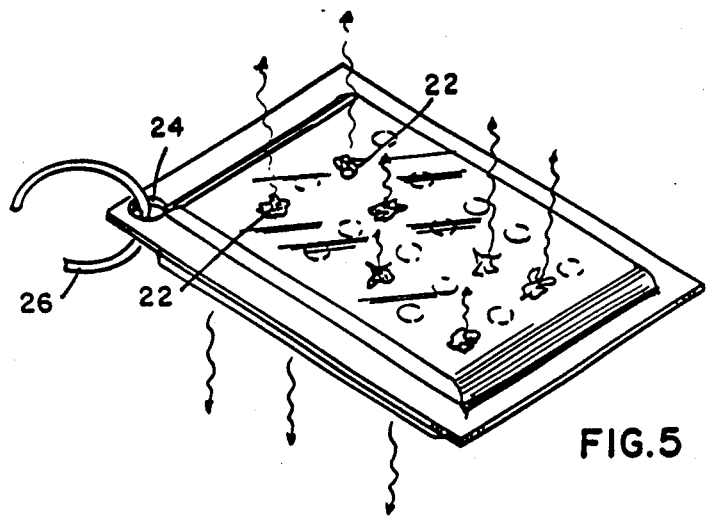
FIG. 5 is a plan view of the package embodying the invention which has been punctured to release the repellent composition material contained within.
Figure 8:
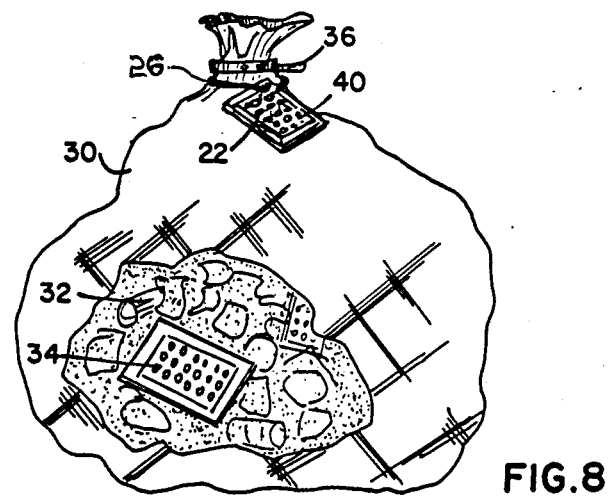
FIG. 8 is a plan view partially broken away illustrating the uses of the invention for a typical trash bag.

Referring now to FIGS. 3, 4 and 5, there is illustrated a modified form of the invention. As shown, the porous cover 18 has been omitted. In this embodiment of the invention, the cover 12 is torn open and the absorbent material 16 saturated with a liquid repellent material is deposited in the receptacle to be protected as illustrated in FIG. 8 discussed hereinafter. Alternatively, the outer cover 12, referring now particularly to FIG. 5, can be punctured with a suitable sharp object to provide puncture holes 22 to permit the repellent material impregnated in absorbent material 16 to be released. In this form of the invention, the repellent package 10 can be provided with an eyelet 24 and fastener 26 whereby the punctured repellent package can be attached in a desired location either externally or internally to the receptacle.

Figure 6:
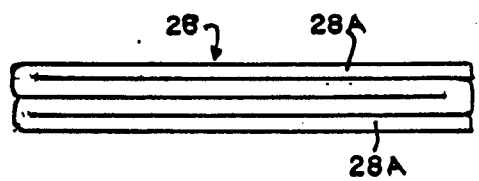
FIG. 6 is a perspective view of a modified form of the inner repellent carrier in folded position.
Figure 7:
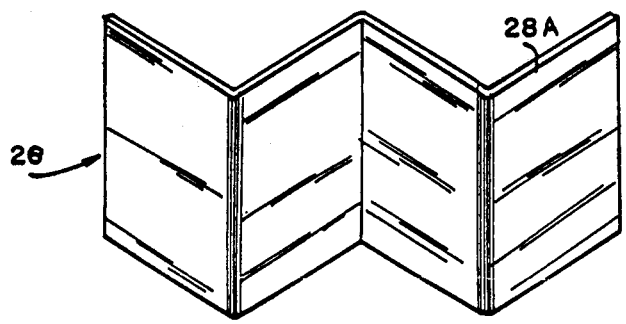
FIG. 7 is a perspective view of the inner repellent carrier of FIG. 6 in a partially unfolded or open position.

The absorbent member may be formed in any suitable fashion, as for example, in the manner shown in FIGS. 6 and 7. As illustrated, the absorbent member, shown generally as 28, may be formed of a sheet of flexible absorbent material such as paper. The sheet 28 may be folded upon itself in sections 28A as shown in FIG. 6. The absorbent member 28 can be saturated with a liquid repellent material prior to or after insertion into outer cover 12 as will be discussed hereinafter. The absorbent member may be compacted in other suitable manners. For example, absorbent paper in crepe or tissue form may be compressed for insertion into outer cover member 12. Where folding of the absorbent material is employed such as described with respect to FIGS. 6 and 7, the folding should be accomplished so that the absorbent member can be easily unfolded when removed from the package to thereby provide a greater surface area to maximize distribution of the impregnated repellent material.

In assembling the pest repellent package, the outer cover may be partially sealed by sealing one or more but not all sides. Thereafter the repellent carrier member may be inserted into the partially sealed cover member. The repellent carrier may be impregnated with the repellent material prior to or after insertion into the cover member. When the repellent carrier is inserted into the cover member before being impregnated, the repellent materials may be injected into the package after insertion of the repellent carrier and the cover member sealed to completely close the package. When the repellent carrier is impregnated prior to insertion into the cover member, the insertion and sealing should be carried out as soon as possible to minimize loss of the repellent composition.

The pest repellent package of the present invention is suitable for use with a variety of types of repellent compositions, such as those disclosed in the prior art U.S. patents discussed hereinabove.

In addition to the disclosed repellent composition of the prior art, I have found that ammonium hydroxide also known as ammonia water provides excellent pest repellent results when used in the strength as sold commercially. I have discovered that the ammonia water does not adversely affect the package covers or the repellent carrier described, is inexpensive, and readily gives off the pungent ammonia vapors.

Figure 9:
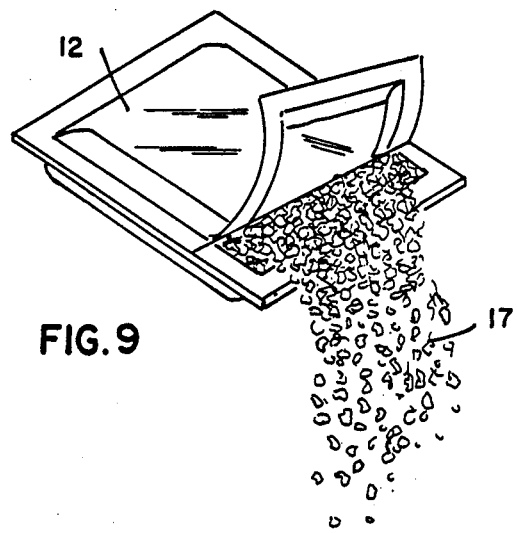
FIG. 9 is a plan view partially broken open illustrating the repellent material carrier as pourable absorbent particulate material.

Referring now to FIG. 9, there is illustrated an alternate embodiment of the invention wherein the repellent carrier material is in the form of small pourable particles 17 formed of a material absorbent to the repellent composition and deposited within the outer cover 12. In this form of the invention, the repellent composition may be released by puncturing the outer cover 12 as described with respect to FIG. 5 or the cover 12 may be torn open and the repellent carrier particles 17 with the absorbed repellent composition poured into the receptacle, as for example the trash bag 30 of FIG. 8, to be protected. The particulate material 17 may be in any suitable granular flake or crystal form, the main requirement being, in addition to these discussed hereinbefore regarding the repellent carrier material, that the particles be pourable. Absorbent granular cellulosic materials are suitable as a particulate repellent composition carrier.

It is to be understood that when the repellent material is in particulate solid form then in accordance with the invention as described with respect to FIGS. 1 and 2, the particles of repellent material can be deposited within the porous inner cover member 18 and enclosed within the outer cover 12. In this form of the invention, the porosity of the cover or size of the holes 20 are selected to have an opening sufficiently small to prevent the repellent particles from passing through. In this case the porous cover may be formed of a thin layer of plastic or paper material having sufficient porosity to maximize the effectiveness of the repellent material.

As mentioned previously the invention has particular utility in providing pest deterrent properties to plastic trash bags typically used in households as trash disposal means.

Referring now to FIG. 8, there is shown various ways in which the pest repellent article of the present invention may be used with a typical plastic trash bag 30 containing various articles of trash 32. As illustrated a repellent carrier 34 of the type disclosed with respect to FIGS. 1 and 2 is removed from the package cover 12 and deposited within the trash bag 30 and the trash bag sealed at the top in the usual manner with twist member 36 which is formed of a length of wire coated with paper or plastic as is well known. In the same manner the repellent carrier 34 can be of the type disclosed with respect to other embodiments of the invention such as, for example, the repellent carriers of FIGS. 2, 5, 6, 7 and 8.

The invention also contemplates the external attachment of repellent articles in accordance with the invention. As shown, a past repellent package 40 containing puncture holes 22 as described with respect to FIG. 5 is attached to the top closure portion of trash bag 30 to provide an external repellent feature. Similarly, inner member 14 of FIG. 1 may be removed and attached in the same manner to provide repellent features.

Figure 10:
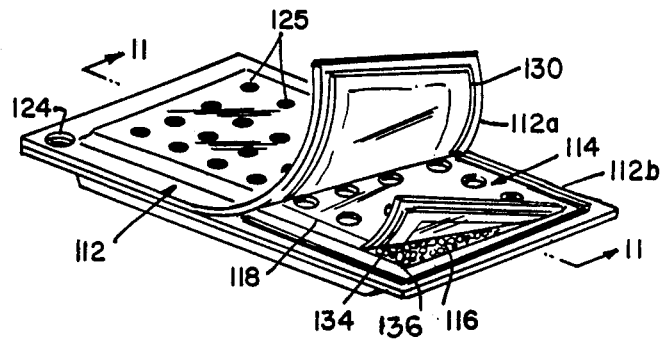
FIG. 10 is a perspective view of an alternate embodiment of the invention partially broken open to illustrate the structure and the inner repellent composition carrier.
Figure 11:
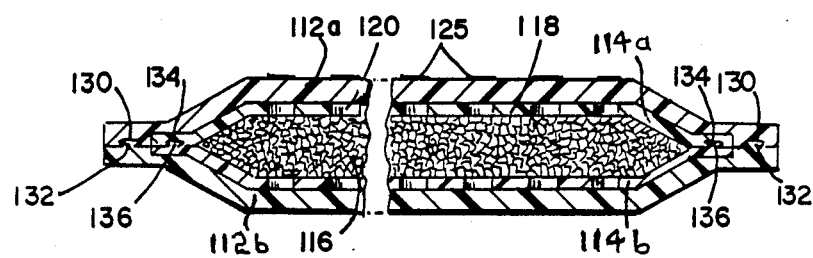
FIG. 11 is a cross-sectional view taken along the lines 11—11 of FIG. 10.

Referring now to FIGS. 10 and 11 of the drawing, there is illustrated an alternate embodiment of a pest repellent article or package in accordance with the present invention. The package comprises an outer cover or envelope 112 which is illustrated as being formed of two generally rectangular members 112a and 112b of the same size and having releasable sealing means disposed about the peripheral edges of members 112a and 112b to provide a completely releasably sealed outer cover 112. As illustrated, a suitable releasable sealing means comprises a slot means 130 disposed about the inner peripheral surface of member 112a and a mating rib means 132 disposed upon the inner peripheral surface of member 112b. In order to form a releasable vapor tight seal, the rib means 132 is pressed into frictional engagement with the slot means 130. The main requirements of the sealing means are that a seal be formed which is releasable and impervious to the pest repellent material and the volatile vapors thereof. Disposed within the outer cover member 112 is a repellent composition material carrier member 114 which is formed of two generally rectangular members 114a and 114b of the same size and having releasable sealing means disposed about the periphery in the same manner as cover 112. Similar to cover 112, the releasable sealing means comprises a slot means 134 disposed about the inner peripheral surface of member 114a and a mating rib means 136 disposed upon the inner peripheral surface of member 114b. The sealing means 134 and 136 operates in the same manner as the sealing means 130 and 132 of cover member 112. Disposed within the repellent material carrier member 114 is a pest repellent carrier material in the form of pourable particles 116 formed of a material absorbent to a volatile pest repellent composition as described hereinbefore with respect to FIG. 9. In this embodiment of the invention, the wall members 114a and 114b are provided with a plurality of holes or apertures 120 to provide a porous pest repellent material carrier. As described hereinbefore, the porosity of the repellent carrier member 114 or the size of the apertures relative to the particle size of the particulate material are selected to have a hole size sufficiently smaller than the size of the particles 116 to prevent the repellent containing particles from passing therethrough. Additionally in accordance with this embodiment of the invention, the outer cover member 112 is provided with indicia means 125 disposed upon the outer surface of the cover. The indicia 125, illustrated as dots, are positioned upon the surface of outer cover 112 at loci so as to be in register with or adjacent to an aperture 120 of the pest repellent material carrier member 114. It can be appreciated that the user may direclty expose one or more of the holes or apertures 120 by simply puncturing the outer cover 112 at a point indicated by the indicia 125 to thereby release the vapors of the volatile repellent material absorbed by the particulate material 116. It can be appreciated that the embodiment of pest repellent articles described and illustrated in FIGS. 10 and 11 provide an article which can be employed in several modes depending upon the desires of the user and the conditions of use. For example, the outer cover 112 can be punctured at the loci of the indicia 125 to expose a sufficient number of apertures 120 depending upon the amount of the volatile pest repellent composition to be released. Also the outer cover members 112a and 112b can be opened by means of the releasable sealing means 130 and 132 and the inner repellent material carrier member 114 removed whereby all of the apertures 120 are exposed to the environment to provide a greater release of the volatile pest repellent composition. Additionally, the discrete particles can be released by means of the releasable sealing means 134 and 136 and poured over an area or within a container to provide greater dispersement of the volatile pest repellent composition as well as treatment of areas not accessible by the pest repellent articles. Additionally, it is to be understood that while the invention has been described with respect to pest repellent articles having a generally rectangular configuration, other configurations such as circular are also contemplated.

While the invention has been described with respect to preferred embodiments, it will be apparent to those skilled in the art that changes and modifications may be made without departing from the scope of the invention herein involved in its broader aspects. Accordingly, it is intended that all matter contained in the above description shall be interpreted as illustrative and not in limiting sense.

What is claimed is:

1. A pest repellent article for dispensing a volatile pest repellent composition comprising:
    an outer envelope member having first and second side members formed of a flexible material impervious to said volatile repellent composition;
    said first and second side members of said outer envelope having corresponding peripheral edges;
    means for releasably sealing the peripheral edges of said outer envelope member comprising:
    a rib means disposed about the peripheral edge of one of said side members; and
    a slot means disposed about the peripheral edge of the other side member;
    said rib means and said slot means forming a releasable pressure-sensitive frictional seal impervious to said volatile repellent composition;
    an inner removable, flexible container member having first and second side members formed of a flexible material;
    said first and second side members of said inner container member having corresponding peripheral edges;
    means for releasably sealing the peripheral edges of said first side member to said second side member of said inner container to form a releasable seal;
    a pest repellent composition carrier disposed within said inner container member;
    said repellent composition carrier being saturated with a volatile pest repellent composition;
    a plurality of apertures disposed in the first and second side members of said inner container member communicating with said pest repellent composition carrier; and
    indicia means disposed upon the outer surface of said first and second side members of said outer envelope;
    said indicia means being in register with adjacent apertures disposed in the first and second sides of said inner container member whereby a puncture of the area of said first and second sides of said outer envelope defined by said indicia measns exposes the adjacent aperture carried by said inner container member to thereby expose said volatile pest repellent composition to the environment.

2. The pest repellent article of claim 1 wherein said repellent composition carrier is formed of discrete particles of absorbent material saturated with volatile pest repellent composition.

3. A pest repellent article for dispensing a volatile pest repellent composition comprising:
    an outer envelope member having first and second side members formed of a flexible material impervious to said volatile repellent composition;
    said first and second side members of said outer envelope having corresponding peripheral edges;
    means for releasably sealing the peripheral edges of said first side member to said second side member of said outer envelope to form a releasable seal impervious to said volatile repellent composition;
    an inner removable, flexible container member having first and second side members formed of a flexible material;
    said first and second side members of said inner container member having corresponding peripheral edges;
    means for releasably sealing the peripheral edges of said inner removable flexible container member comprising:
    a rib means disposed about the peripheral edge of one of said side members; and
    a slot means disposed about the peripheral edge of the other side member;
    said rib means and said slot means forming a releasable pressure-sensitive frictional seal;
    a pest repellent composition carrier disposed within said inner container member;
    said repellent composition carrier being saturated with a volatile pest repellent composition;
    a plurality of apertures disposed in the first and second side members of said inner container member communicating with said pest repellent composition carrier; and
    indicia means disposed upon the outer surface of said first and second side members of said outer envelope;
    said indicia means being in register with adjacent apertures disposed in the first and second sides of said inner container member whereby a puncture of the area of said first and second sides of said outer envelope defined by said indicia means exposes the adjacent aperture carried by said inner container member to thereby expose said volatile pest repellent composition to the environment.

4. The pest repellent article of claim 3 wherein said repellent composition carrier is formed of discrete particles of absorbent material saturated with volatile pest repellent composition.

* * * * *